United States Patent [19]

Barnard

[11] Patent Number: 4,870,961
[45] Date of Patent: Oct. 3, 1989

[54] MEDICAL VENTILATOR TUBE AND MANIFOLD ASSEMBLY

[76] Inventor: Gordon D. Barnard, P.O. Box 60942, Oklahoma City, Okla. 73146

[21] Appl. No.: 909,593

[22] Filed: Sep. 22, 1986

[51] Int. Cl.$^4$ .............................................. A62B 9/04
[52] U.S. Cl. .......................... 128/202.27; 128/204.18; 285/70; 137/547
[58] Field of Search .................... 128/202.27, 204.18, 128/205.13, 204.21, 204.23, 205.12, 205.14, 205.15, 205.16, 205.17, 911, 912, 203.12, 203.25, 202.13, 204.13, 201.28; 604/905

[56] References Cited

U.S. PATENT DOCUMENTS

| | | | |
|---|---|---|---|
| 2,302,707 | 11/1942 | Mejean | 128/185 |
| 2,482,292 | 9/1949 | Sabbia | 244/122 |
| 3,158,164 | 11/1964 | Barton | 137/884 |
| 3,394,954 | 7/1968 | Sarns | 285/319 |
| 3,486,730 | 12/1969 | Potash | 251/149.7 |
| 3,831,599 | 8/1974 | Needham | 128/203.12 |
| 3,888,518 | 6/1975 | Delessert | 285/70 |
| 3,901,230 | 8/1975 | Henkin | 128/205.17 |
| 4,076,285 | 2/1978 | Martinez | 285/332 |
| 4,187,846 | 2/1980 | Lolachi et al. | 128/214 R |
| 4,232,666 | 11/1980 | Savelli et al. | 128/203.28 |
| 4,366,816 | 1/1983 | Bayard et al. | 128/213 A |
| 4,367,888 | 1/1983 | Leverberg et al. | 285/28 |
| 4,378,795 | 4/1983 | Feathers et al. | 128/202.27 |
| 4,418,945 | 12/1983 | Kellogg | 604/905 |
| 4,458,841 | 7/1984 | Laakaniemi et al. | 137/209 |
| 4,602,658 | 7/1986 | Luther et al. | 137/614.02 |
| 4,651,728 | 3/1987 | Gupta et al. | 128/201.28 |

FOREIGN PATENT DOCUMENTS

| | | | |
|---|---|---|---|
| 3336578 | 4/1985 | Fed. Rep. of Germany | 128/203.12 |
| 1148418 | 12/1957 | France | 128/202.27 |
| 2164572 | 3/1986 | United Kingdom | 128/204.18 |

OTHER PUBLICATIONS

Model MA-1 manufactured by Puritan-Bennett Corporation of California—Operating Instructions, pp. 10, 44–47.
Models MA-2 and MA 2+2 manufactured by Puritan-Bennett Corporation of California, Operating Instructions, pp. 54–56.
Hospal Model 225/SIMV manufactured by Hospal Medical Corporation—Operators Manual, pp. 2, 3.
Monaghan 225 available from Monaghan Division of Sandoz-Wander, Inc., of Littleton, Colorado—Operator's Manual, pp. 8, 9.

Primary Examiner—Max Hindenburg
Assistant Examiner—K. M. Reichle
Attorney, Agent, or Firm—Laney, Dougherty, Hessin & Beavers

[57] ABSTRACT

A medical ventilator tube and manifold assembly. The assembly is used to connect between a patient breathing tube and a medical ventilator machine used in providing assistance to a patient for breathing. The tube and manifold assembly provides a quick-change patient ventilator circuit which allows a plurality of tubing connections to be disconnected and reconnected simultaneously so that a portion of the ventilator circuit may be removed for sterilization and quickly replaced, thus minimizing danger to the patient. The ventilator circuit includes a ventilator machine manifold and a circuit manifold connectable to the ventilator machine manifold. A latch is provided for securely holding the manifolds together. The necessary tubing connections are made between the patient breathing tube and the circuit manifold and between the medical ventilator and the ventilator machine manifold. The manifolds have a plurality of sealingly separated passageways therethrough which are connected to the corresponding tubing.

20 Claims, 3 Drawing Sheets

FIG. 7

MEDICAL VENTILATOR TUBE AND MANIFOLD ASSEMBLY

BACKGROUND OF THE INVENTION

1. Field Of The Invention

The present invention relates to medical ventilator devices for providing breathing assistance for patients, and more particularly, to a ventilator circuit formed by a tube and manifold assembly providing connections between a medical ventilator and the patient.

2. Description Of The Prior Art

Medical ventilator devices are well known in the art and are commonly used with patients whose breathing is sufficiently impaired that mechanical assistance is needed. The most commonly used medical ventilators are of a positive pressure type wherein a mechanical lung cyclically forces air through an inhalation tube.

Following each inhalation, the pressure of the air in the patient's lungs, combined with the elastic recoil properties of the chest wall and lungs, create a pressure gradient which passively causes exhalation through an exhalation tube. The inhalation and exhalation tubes together with other pathways for air traveling to and from the patient form the ventilator circuit.

To accomplish the inhalation and exhalation, a closed, or gas-tight, system of circuit tubing is required. In addition to the inhalation and exhalation tubes, a patient breathing tube must be sealingly connected to the patient's mouth or trachea. This patient breathing tube is then sealingly connected to the inhalation and exhalation tubes which are in turn sealingly connected to the medical ventilator machine. The mechanical lung of the medical ventilator is controlled by a master control device.

To properly control the inhalation and exhalation phases, the master control device utilizes an exhalation valve disposed on the exhalation tube for allowing pressure to be contained during an inhalation phase. The exhalation valve opens during the exhalation phase. The control of this valve by the medical ventilator is accomplished by a pneumatic signal which is conveyed from the ventilator master control device to the exhalation valve by means of an exhalation valve drive tube.

The pressure within the tubing system is monitored by means of a patient air pressure tube which is connected from a position adjacent the patient breathing tube to a pressure sensor on the medical ventilator for communicating this pressure level to the machine. Based on this pressure signal, the medical ventilator can acutate an emergency signal if patient pressure is lost or reduced below a predetermined or set level.

Many medical ventilator machines also incorporate a nebulizer device for introducing regulated amounts of medicine into the air being delivered to the patient through the inhalation tube. The nebulizer is disposed on the inhalation tube pathway and is controlled pneumatically by the master control device. A pneumatic signal controlling the nebulizer and regulating the flow of medication enhanced air is conveyed from the ventilator master control device to the nebulizer by means of a nebulizer drive or control tube connected therebetween.

Medical ventilator machines may also incorporate a means for warming and humidifying the air delivered to the patient. As air flows through the circuit tubing, the warm, moist air condenses in the tubing, and bacteria can grow in this warm and moist environment. If the bacteria is communicated to the patient, an infection can result, and therefore it is necessary to replace or change out the tubing frequently. The changed-out tubing can be sterilized or discarded.

The disconnection, replacement and reconnection of all of the tubing in the ventilator circuit can be dangerous for the patient because many mechanically ventilated patients are dependent on the ventilator for each and every breath they take. Any significant interruption in the breathing cycle can prove harmful to them. This is of extreme importance for critically ill patients who may have no respiratory function other than that provided by the medical ventilator.

As described above, as many as five different tubes or hoses must be replaced in the process of changing out the ventilator circuit tubing. These tubes include the inhalation tube, the exhalation tube, the exhalation valve drive tube, the patient air pressure tube and the nebulizer drive tube. Since each of these tubes has two ends, it will be seen that as many as ten different connections and disconnections can be required for a complete change-out procedure. Making this many connections and disconnections can prove dangerous to the patient as already mentioned. In addition, accidental disconnection can also prove to be dangerous.

The medical ventilator tube and manifold assembly of the present invention solves these problems by providing a ventilator circuit which is more easily connected and disconnected while still insuring secure attachment at all connection sites. Further, the present invention provides a much less time-consuming method of changing out ventilation circuit tubing and is thus safer for the patient.

SUMMARY OF THE INVENTION

The medical ventilator tube and manifold assembly of the present invention provides a quick-change patient ventilator circuit comprising first manifold means and first tubing means for interconnecting the first manifold means and a medical ventilator. The first manifold means and first tubing means define a plurality of first flow passageway means therethrough.

The ventilator circuit also comprises second manifold means and second tubing means for interconnecting the second manifold means and a patient breathing tube. The second manifold means is adapted for detachable connection with the first manifold means such that the first and second manifold means have a connected operating position. The second manifold means and second tubing means define a plurality of second flow passageway means therethrough. The first flow passageway means are in corresponding communication with the second flow passageway means when the first and second manifold means are in the operating position.

In the preferred embodiment, the first tubing means includes humidifier means for humidifying air flowing through at least one of the first passageway means from the medical ventilator.

The second tubing means preferably includes valve means for controlling exhaled air from the patient breathing tube and valve drive tubing means for communicating an air signal from the medical ventilator to the valve means.

The second tubing means also preferably includes nebulizer means for providing medication to air which is directed to the patient breathing tube from the medical ventilator and nebulizer tubing means for communicating another air signal from the medical ventilator to the nebulizer means.

The ventilator circuit further preferably comprises patient pressure tubing means for communicating air pressure adjacent the patient breathing tube to the medical ventilator.

The first manifold means is preferably in the form of a ventilator machine manifold, and the first tubing means includes a first inhalation tube, a spirometer tube, a first exhalation valve drive tube, a first patient pressure tube and a first nebulizer drive or control tube. The first flow passageway means are formed by these tubes and corresponding passageways defined through the ventilator machine manifold.

The second manifold means is characterized by a circuit manifold latchably connectable to the ventilator machine manifold, and the second tubing means includes a second inhalation tube, an exhalation tube, a second exhalation valve drive tube, a second patient pressure tube and a second nebulizer drive or control tube. The second flow passageway means is formed by these tubes and corresponding passageways defined through the circuit manifold.

The valve means is best characterized by an exhalation valve on the exhalation tube. The nebulizer means includes a nebulizer mounted on the second inhalation tube.

Latching means are provided for the manifold means. Preferably, one of the first and second manifold means includes a latch receiver and the other of the manifold means includes a latch which is latchably receivable in the latch receiver.

Sealing means is provided for sealing between the ventilator machine and circuit manifolds when in the operating position.

Hygroscopic filtering means may be placed in any of the tubing means in the circuit or in either manifold means for filtering air flow therethrough in a manner known in the art.

An important object of the invention is to provide a ventilator circuit which can be more easily connected and disconnected during a change-out procedure while still insuring secure attachment at all connection sites.

Another object of the invention is to provide a much less time-consuming method of changing out tubing between a patient and a medical ventilator assembly such that a change-out procedure is safer for the patient.

A further object of the invention is to provide a ventilator circuit with a plurality of simultaneously changeable tubing connections.

Still another object is to provide a ventilator circuit having connectable first and second manifold means.

Additional objects and advantages of the invention will become apparent as the following detailed description of the preferred embodiment is read in accordance with the drawings which illustrate such preferred embodiment.

DESCRIPTION OF THE PREFERRED EMBODIMENT

Figure 1:
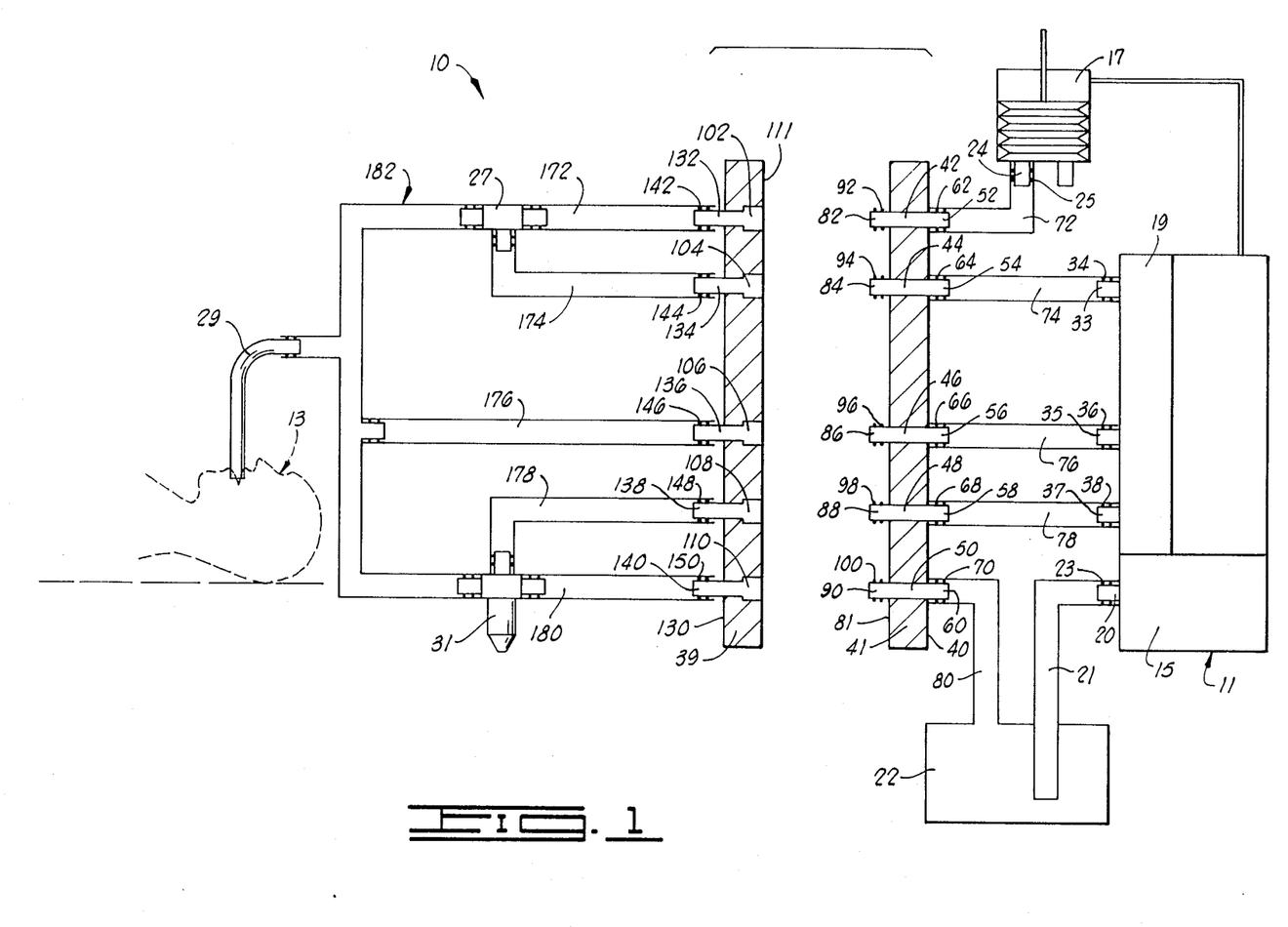
FIG. 1 is a schematic of the tube and manifold assembly of the present invention providing a ventilator circuit connected between a medical ventilator machine and a patient breathing tube.

Referring now to the drawings, and more particularly to FIG. 1, the medical ventilator tube and manifold assembly of the present invention is shown and generally designated by the numeral 10 as forming a ventilator circuit between a medical ventilator machine 11 and a patient 13.

Ventilator machine 11 is of a conventional positive pressure type. Ventilator machine 11 includes a pressurized air supply device 15, a spirometer 17 and a pneumatic control device 19. An example of a ventilator machine 11 is a Bennett MA- 2 Model manufactured by Puritan-Bennett Corporation.

Pressurized air supply device 15 of ventilator machine 11 has an inhalation tube fitting 20 extending therefrom. A tube 21 interconnects inhalation tube fitting 20 with a humidifier 22 which is used to humidify the air to the patient. Sealing means 23 are provided between tube fitting 20 and tube 21.

Spirometer 17 measures the volume of air exhaled from the lungs of patient 13 connected to ventilator machine 11. If the volume of exhaled air measured by spirometer 17 falls below a predetermined or set level, a warning signal is generated by ventilator machine 11 to indicate that a system malfunction or circuit leak has occurred. A spirometer inlet fitting 24 with sealing means 25 thereon is provided on spirometer 17 for connecting the spirometer to the exhalation portion of tube and manifold assembly 10 of the ventilator circuit, as will be hereinafter described.

Pneumatic control device 19 of medical ventilator 11 actuates or receives three pneumatic signals. The first pneumatic signal operates exhalation valve 27. By means of this first signal, exhalation valve 27 controls the flow of exhaled air during the inhalation and exhalation phases of the patient ventilation.

The second signal is a pressure signal from a position adjacent patient breathing tube 29. Patient breathing tube 29 is inserted directly into the airway or trachea of patient 13 and, therefore, the second signal indicates the air pressure adjacent the patient's lungs. A warning signal is actuated by ventilator machine 11 if the patient pressure falls below a predetermined or set level as determined by the second signal and control device 19.

The third signal actuates a nebulizer 31. Nebulizer 31 injects medication into the air to be inhaled by patient 13, and thus the third pressure signal controls the amount of medication delivered to the air.

Pneumatic control device 19 has tube fittings 33, 35 and 37 with sealing means 34, 36 and 38 thereon, respectively. Tube fittings 33, 35 and 37 are used for connecting tubes to pneumatic control device 19 of medical ventilator 11 through which the first, second and third pneumatic signals, respectively, are conveyed.

Spirometer 17, pressurized air supply device 15 and the signals of pneumatic control device 19 are all responsive to a master control device in ventilator machine 11. The master control device allows an operator to control the operation of ventilator machine 11 for safe patient ventilation depending upon the size, physical condition, etc., of the patient.

The above-described fittings and devices are conventional and known in the art. In a typical set-up for a ventilator machine 11, these conventional fittings and devices would be each connected in a circuit of separate tubes. Each of these separate tubes conventionally requires frequent connection and disconnection so that cleaning and sterilization of the tubes can be carried out. Tube and manifold assembly 10 of the present invention provides an integral ventilator circuit, the tubes of which are all joined to a circuit manifold 39 which, in turn, is detachably connected to a ventilator machine manifold 41 tubed to medical ventilator 11. As will be seen, this arrangement allows a single junction between the entire tube and manifold assembly 10 and ventilator machine 11. The single junction allows a greatly improved method of connecting and disconnecting the tubes for cleaning and sterilization.

Ventilator machine manifold 41 is preferably located adjacent fittings 33, 35 and 37 on pneumatic control device 19 and also adjacent humidifier 22 and spirometer 17. This allows short tubing connections between ventilator machine manifold 41 and ventilator machine 11.

Ventilator machine manifold 41 defines a plurality of substantially cylindrical passageways 42, 44, 46, 48 and 50 therethrough. On ventilator machine side 40 of passageways 42, 44, 46, 48 and 50 are tube fittings 52, 54, 56, 58 and 60, respectively. Tube fittings 52, 54, 56, 58 and 60 include sealing means 62, 64, 66, 68 and 70 thereon, respectively, for sealing attachment of tubes thereto.

A spirometer tube 72 is attached to spirometer inlet fitting 24 and tube fitting 52 for connecting passageway 42 to spirometer 17.

A first exhalation valve drive tube 74 is attached to tube fittings 33 and 54, thus connecting pneumatic control device 19 to passageway 44.

A first patient pressure tube 76 is attached to tube fittings 35 and 56, thus interconnecting pneumatic control device 19 and passageway 46.

A first nebulizer drive or control tube 78 is attached to tube fittings 37 and 58 which provides a connection between pneumatic control device 19 and passageway 48.

Finally, a first inhalation tube 80 extends from humidifier 22 and is attached to tube fitting 60 to provide a connection between the humidifier and passageway 50.

On patient side 81 of passageways 42, 44, 46, 48 and 50 are a plurality of tube fittings 82, 84, 86, 88 and 90, respectively, and each of these tube fittings has respective sealing means 92, 94, 96, 98 and 100.

Circuit manifold 39 defines a plurality of passageways 102, 104, 106, 108 and 110 therethrough which correspond to passageways 42, 44, 46, 48 and 50 in ventilator machine manifold 41. On machine side 111 of circuit manifold 39, passageways 102, 104, 106, 108 and 110 have enlarged portions which are adapted for receiving tube fittings 82, 84, 86, 88 and 90, respectively. Thus, circuit manifold 39 matingly joins with ventilator machine manifold 41 in a connected operating position in which passageways 42 and 102, passageways 44 and 104, passageways 46 and 106, passageways 48 and 108 and passageways 50 and 110 are interconnected. Sealing means 92, 94, 96, 98 and 100 provide positive sealing at the junction between the respective passageways when circuit manifold 39 and ventilator machine manifold 41 are in this operating position.

Figure 2:
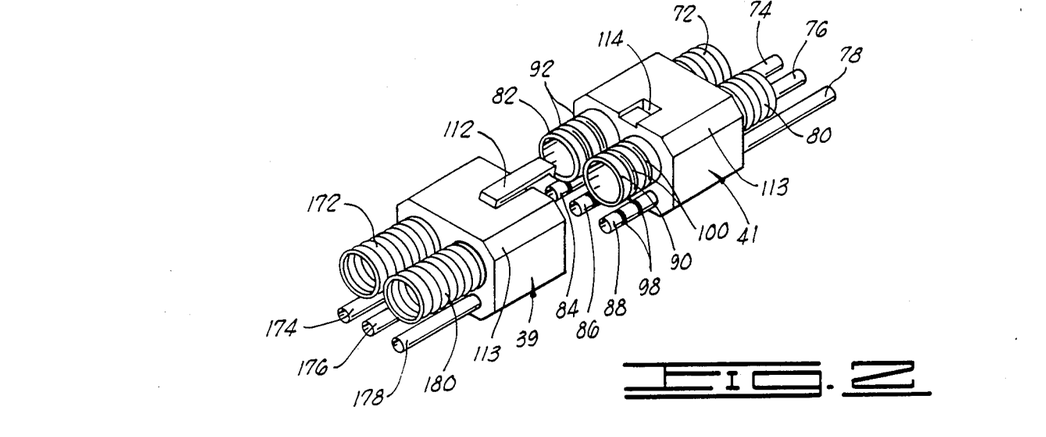
FIG. 2 is a perspective view of a portion of a preferred embodiment of the tube and manifold assembly illustrated in a disconnected position.
Figure 3:
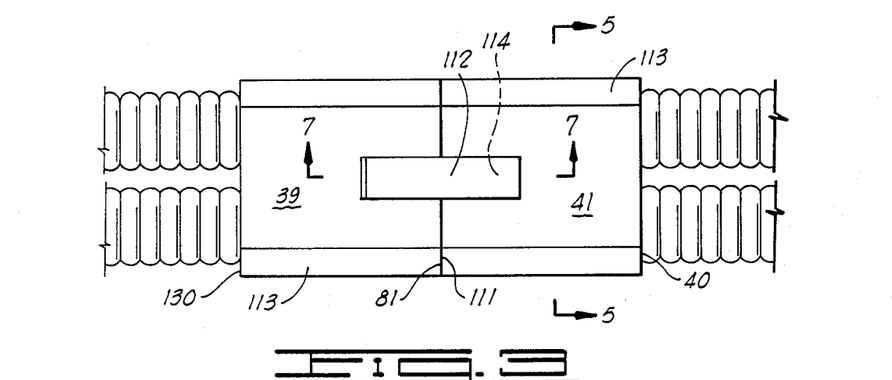
FIG. 3 shows a top view of a portion of the apparatus shown in a connected position.
Figure 4:
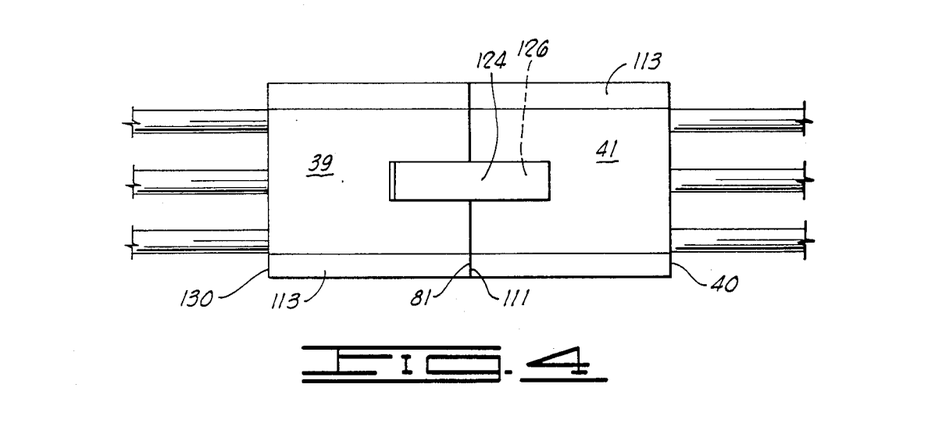
FIG. 4 is a bottom view of a portion of the apparatus.
Figure 5:
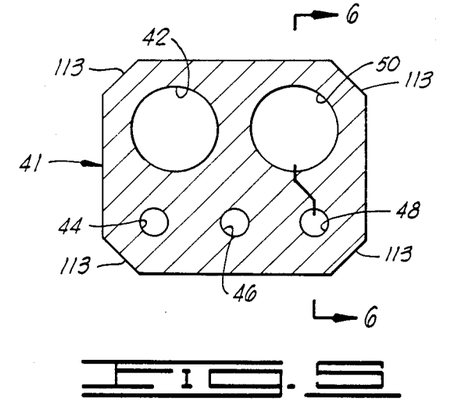
FIG. 5 is a cross section taken along lines 5—5 in FIG. 3.
Figure 6:
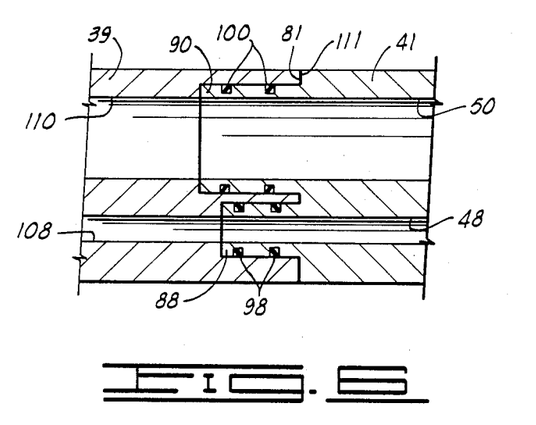
FIG. 6 is a cross section taken along lines 6—6 in FIG. 5.

Referring now to FIGS. 2-7, details of manifolds 39 and 41, and the connections therebetween, are illustrated. As best seen in FIGS. 2, 5 and 6, passageways 50 and 110 corresponding to inhalation tube 80 and passageways 42 and 102 corresponding to spirometer tube 72 are relatively larger than passageways 44 and 104 corresponding to first exhalation valve drive tube 74, passageways 46 and 106 corresponding to first patient pressure tube 76 and passageways 48 and 108 corresponding to first nebulizer drive or control tube 78. The sizes vary because of the relatively larger volume of air which passes through inhalation tube 80 and spirometer tube 72.

In the preferred embodiment, the larger passageways are disposed adjacent each other and extend through an upper portion of circuit manifold 39 and ventilator machine manifold 41. The smaller passageways are all disposed substantially parallel to and beneath the larger passageways. This configuration of large and small passageways in circuit manifold 39 and ventilator machine manifold 41 allows a compact and easily held manifold exterior for each of manifold 39 and 41. In the embodiment shown in FIGS. 2-7, the exteriors of manifolds 39 and 41 are approximately rectangular in shape with beveled corners 113. However, it is not intended that the invention be limited to this particular configuration, and it will be obvious to those skilled in the art, that other shapes, such as cylindrical, would also work well.

Figure 7:
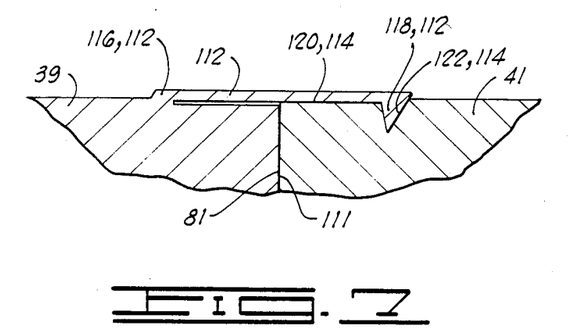
FIG. 7 is a cross section taken along lines 7—7 in FIG. 3.

Referring now to FIGS. 2 and 7, the upper side of circuit manifold 39 has an elongated latch 112 extending therefrom, and the upper side of ventilator machine manifold 41 defines a latch receiver 114 thereon, thus providing latching means. Latch 112 includes a base portion 116 attached to circuit manifold 39 and spaced inwardly from machine side 111 of the circuit manifold. Latch 112 also includes a downwardly directed V-shaped engaging portion 118 at the distal end thereof. Latch receiver 114 is in the form of a groove defined in ventilator machine manifold 41, and the groove includes a relatively flat portion 120 and a V-shaped portion 122 spaced from patient side 81 of the ventilator machine manifold and corresponding to V-shaped engaging portion 118 of latch 112. Latch 112 is resiliently received in latch receiver 114 for locking circuit manifold 39 to ventilator machine manifold 41 when the manifolds are sealingly mated together in the operating position. As shown in FIG. 4, a similar latch 124 extends from the bottom side of circuit manifold 39 and fits into a similar latch receiver 126 on the bottom side of ventilator machine manifold 41. Finger pressure on latches 112 and 124 coordinated with hand pressure used to separate circuit manifolds 39 and ventilator machine manifold 41 will unlock latches 112 and 124 from latch receivers 114 and 126, respectively, resulting in disconnection of circuit manifold 39 from ventilator machine manifold 41. Circuit manifold 39 and ventilator machine manifold 41 are preferably formed of plastic with latches 112 and 114 integrally formed with circuit manifold 39. It will be seen by those skilled in the art that the location of the latches and latch receivers could be reversed such that at least one latch could extend from ventilator machine manifold 41 and be received in a latch receiver on circuit manifold 39. The use of plastic results in resilient latches 112 and 124, and also plastic is a light, easily molded material which is also easily sterilized.

Preferably, tube fittings 82, 84, 86, 88 and 90 are integrally formed with ventilator machine manifold 41. However, the apparatus would work just as easily if these tube fittings were integrally formed with circuit manifold 39. Also, tube fittings 52, 54, 56, 58 and 60 are preferably integrally formed with ventilator machine manifold 41.

Referring again to FIG. 1, a patient side 130 of circuit manifold 39 has a plurality of tube fittings 132, 134, 136, 138 and 140 extending therefrom, these tube fittings having sealing means 142, 144, 146, 148 and 150 thereon, respectively. Tube fittings 132, 134, 136, 138 and 140 are preferably integrally formed with circuit manifold 39 and are in communication with passageways 102, 104, 106, 108 and 110, respectively, in the circuit manifold.

Thus, an exhalation tube 172 may be placed in communication with passageway 102 and a second exhalation valve drive tube 174 may be placed in communication with passageway 104. Exhalation tube 172 and second exhalation valve drive tube 174 are connected to exhalation valve 27. Exhalation valve 27 controls air flow from patient breathing tube 29 through exhalation tube 172 and thus through spirometer tube 72.

A second patient pressure tube 176 provides communication between patient breathing tube 29 and passageway 106. It will be seen that second patient pressure tube 176 is in communication with first patient pressure tube 76.

A second nebulizer drive or control tube 178 provides communication between nebulizer 31 and passageway 108, and a second inhalation tube 180 provides communication between the nebulizer and passageway 110. It will be seen that second nebulizer drive tube 178 is in communication with first nebulizer drive tube 78, and second inhalation tube 180 is in communication with first exhalation tube 80 from humidifier 22. Nebulizer 31 dispenses appropriate medication into the air passing through first and second inhalation tubes 80 and 180.

Circuit manifold 39 and all of the tubes connected between it and patient breathing tube 39 form a circuit, generally designated by the numeral 182. Circuit 182 thus forms an integral unit which can be replaced or traded out in a single, simple operation. This allows a sterile, replacement circuit 182 to be easily substituted for a contaminated circuit 182. With a circuit 182 in place connected to patient breathing tube 29 and having circuit manifold 39 matingly attached to ventilating machine manifold 41, a replacement procedure in accordance with the present invention requires only that latches 112 and 124 be released, circuit manifold 39 be removed from ventilator machine manifold 41, circuit 182 be disconnected from patient breathing tube 29 and a new sterile circuit 182 be connected by matingly joining the new circuit manifold 39 to ventilator manifold 41 and reconnecting to patient breathing tube 29.

Although circuit 182 is described as individually connected tubes, it will be seen by those skilled in the art that circuit 182 can be easily formed entirely of a single disposable piece. If circuit 182 is not formed of a single piece, the connections in the circuit obviously can be made secure by clamps or the like so that accidental disconnection of the various tubes is minimized.

Hygroscopic filters may be disposed in any of the tubes or either circuit manifold 39 or ventilator machine manifold 41 so that air flow therethrough may be filtered in a manner known in the art.

It will be seen, therefore, that the medical ventilator tube and manifold assembly of the present invention is well adapted to carry out the ends and advantages mentioned, as well as those inherent therein. While a presently preferred embodiment of the invention has been described for the purposes of this disclosure, numerous changes in the arrangement and construction of parts can be made by those skilled in the art, which changes are encompassed within the scope and spirit of the invention as defined by the appended claims. The foregoing disclosure and showings made in the drawings are merely illustrative of the principles of this invention and are not to be interpreted in a limiting sense.

What is claimed is:

1. A quick-change ventilator circuit for use for interconnecting a medical ventilator, of the type adapted for providing breathing assistance to a patient, with a patient breathing tube, said circuit comprising:
   first manifold means;
   first tubing means for connecting said first manifold means to the medical ventilator, said first manifold means and said first tubing means defining a plurality of first flow passageway means therethrough;
   second manifold means for detachably connecting to aid first manifold means such that said first and second manifold means have a connected operating position; and
   second tubing means for connecting said second manifold means to the patient breathing tube, said second manifold means and said second tubing means defining a plurality of second flow passageway means therethrough, wherein said first flow passageway means are in corresponding fluid communication with said second flow passageway means when said first and second manifold means are in said operating position.

2. The circuit of claim 1 wherein said first tubing means includes humidifier means for humidifying air flowing through at least one of said first passageway means.

3. The circuit of claim 1 wherein said second tubing means includes valve means for controlling exhaled air flowing through said second tubing means from the patient breathing tube.

4. The circuit of claim 3 further comprising valve drive tubing means for connecting said valve means to the medical ventilator and for communicating an air signal from the medical ventilator to said valve means.

5. The circuit of claim 1 wherein said second tubing means includes nebulizer means for providing medication to air flowing through said second tubing means.

6. The circuit of claim 5 further comprising nebulizer tubing means for connecting said nebulizer means to the medical ventilator and for communicating an air signal from the medical ventilator to said nebulizer means.

7. The circuit of claim 1 further comprising patient pressure tubing means for connecting the ventilator to the patient breathing tube and for communicating air pressure adjacent the patient breathing tube to the ventilator.

8. A replaceable medical ventilator tube and manifold assembly for simultaneously connecting a patient breathing tube with components of a medical ventilator machine for providing breathing assistance to a patient including a pressurized air supply device, a spirometer and a pneumatic control device, said tube and manifold assembly comprising:

a tubing circuit comprising:
an inhalation tube having means for connecting to the patient breathing tube;
an exhalation tube having means for connecting to the patient breathing tube;
an exhalation valve means connected to said exhalation tube for allowing exhalation through said exhalation tube responsive to an air signal from the pneumatic control device on the medical ventilator machine; and
an exhalation valve drive tube connected to said exhalation valve means for conveying the air signal thereto; a circuit manifold defining:
an inhalation passageway connected to said inhalation tube;
an exhalation passageway connected to said exhalation tube; and
an exhalation valve drive tube passageway connected to said exhalation valve drive tube; and
a ventilator machine manifold for positioning adjacent the medical ventilator machine and detachably connected to said circuit manifold, said ventilator machine manifold defining:
an inhalation passageway having means for connecting to the pressurized air supply device on the medical ventilator machine and being positioned in said manifold so as to be in fluid communication with said inhalation passageway in said circuit manifold when said ventilator machine manifold and said circuit manifold are connected;
an exhalation passageway having means for connecting to the spirometer and being positioned in said manifold so as to be in fluid communication with said exhalation passageway in said circuit manifold when said ventilator machine manifold and said circuit manifold are connected; and
an exhalation drive tube passageway having means for connecting to the pneumatic control device and being positioned in said manifold so as to be in fluid communication with said exhalation drive tube passageway in said circuit manifold when said ventilator machine manifold and said circuit manifold are connected.

9. The tube and manifold assembly of claim 8 wherein:
said tubing circuit further comprises:
a nebulizer connected to said inhalation tube; and
a nebulizer tube connected to said nebulizer;
said circuit manifold further defines a nebulizer passageway connected to said nebulizer tube; and
said ventilator manifold further defines a nebulizer passageway having means for connecting to the pneumatic control device on the medical ventilator machine and being positioned in said manifold so as to be in fluid communication with said nebulizer passageway of said circuit manifold when said ventilator machine manifold and said circuit manifold are connected.

10. The tube and manifold assembly of claim 8 wherein:
said tubing circuit further comprises a patient pressure tube having means for positioning adjacent the patient breathing tube;
said circuit manifold further defines a patient pressure passageway connected to said patient pressure tube; and
said ventilator machine manifold further defines a patient pressure passageway having means for connecting to the pneumatic control device on the medical ventilator machine and being positioned in said manifold so as to be in fluid communication with said patient pressure passageway of said circuit manifold when said ventilator machine manifold and said circuit manifold are connected.

11. The tube and manifold assembly of claim 8 wherein said ventilator machine and circuit manifolds are generally of rectangular shape with said passageways extending longitudinally therethrough.

12. The tube and manifold assembly of claim 8 wherein said ventilator machine manifold and circuit manifolds include latch means for temporarily locking said manifolds in the connected position.

13. The tube and manifold assembly of claim 8 further comprising sealing means for sealing between said ventilator machine and circuit manifolds when said manifolds are connected.

14. A replaceable medical ventilator circuit assembly for use in connecting a patient breathing tube and a humidifier to a medical ventilator of the type having a pressurized air supply device, a spirometer, a pneumatic control device with first, second and third pressure signal fittings thereon, said circuit assembly comprising:
a single ventilator manifold defining:
an inhalation passageway;
an exhalation passageway;
an exhalation valve means drive passageway;
a patient pressure passageway; and
nebulizer means passageway;
a first inhalation tube having means for connecting said inhalation passageway to the humidifier and the medical ventilator;
a spirometer tube having means for connecting said exhalation passageway to the spirometer on the medical ventilator;
a first exhalation valve means drive tube having means for connecting said exhalation valve means drive passageway to the first pressure signal fitting on the pneumatic control device of the medical ventilator;
a first patient pressure tube having means for connecting said patient pressure passageway to the second pressure signal fitting on the pneumatic control device;
a first nebulizer means drive tube having means for connecting pressure signal fitting on the pneumatic control device;
a single circuit manifold removably attached to said ventilator manifold such that said ventilator manifold and said circuit manifold have a connected operating position wherein all connections to the ventilator are connected simultaneously and a disconnected position wherein all of said connections to said ventilator are disconnected simultaneously, said circuit manifold defining:
an inhalation passageway being positioned in said circuit manifold so as to be in fluid communication with said inhalation passageway of said ventilator manifold when said manifolds are in said operating position;
an exhalation passageway being positioned in said circuit manifold so as to be in fluid communication with said exhalation passageway of said ventilator manifold when said manifolds are in said operating position;

an exhalation valve means drive passageway being positioned in said circuit manifold so as to be in fluid communication with said exhalation valve means drive passageway of said ventilator manifold when said manifolds are in said operating position;

a patient pressure passageway being positioned in said circuit manifold so as to be in fluid communication with said patient pressure passageway of said ventilator manifold when said manifolds are in said operating position; and a nebulizer means passageway being positioned in said circuit manifold so as to be in fluid communication with said nebulizer means passageway of said ventilator manifold when said manifolds are in said operating position;

a second inhalation tube having means for connecting said inhalation passageway of said circuit manifold to the patient pressure breathing tube;

a nebulizer means for controlling flow of medication into said second inhalation tube;

an exhalation tube having means for connecting said exhalation passageway of said circuit manifold to the patient breathing tube;

an exhalation valve means for controlling flow of exhaled air through said exhalation tube;

a second exhalation valve means drive tube connecting said exhalation valve means drive passageway of said circuit manifold to said exhalation valve means;

a second patient pressure tube having means for connecting said patient pressure passageway of said circuit manifold to the patient breathing tube; and a second nebulizer means drive tube connecting said nebulizer means passageway of said circuit manifold to said nebulizer means.

15. The circuit assembly of claim 14 wherein said inhalation and exhalation passageways of said manifolds are relatively larger than said exhalation valve means drive, patient pressure and nebulizer means drive passageways.

16. The circuit assembly of claim 15 wherein:
said inhalation and exhalation passageways are adjacent one another; and
said exhalation valve means drive, patient pressure and nebulizer means drive passageways are substantially parallel to said inhalation and exhalation passageways.

17. The circuit assembly of claim 14 further comprising latching means for latchably connecting said ventilator and circuit manifolds in said operating position.

18. The circuit assembly of claim 17 wherein said latching means is characterized by:
one of said ventilator machine and circuit manifolds including a latch receiver; and
the other of said ventilator machine and circuit manifolds including an elongated latch extending therefrom and detachably received in said latch receiver.

19. The circuit assembly of claim 18 wherein:
said latch includes a V-shaped engaging portion; and
said latch receiver includes:
a V-shaped groove corresponding to said V-shaped portion of said latch; and
a relatively flat portion between the groove and the other of said ventilator and said circuit manifolds 20. The circuit assembly of claim 14 further comprising sealing means for sealing said connections to the ventilator machine and for sealing the connections to said ventilator machine and circuit manifolds when in said operating position.

* * * * *

UNITED STATES PATENT AND TRADEMARK OFFICE
CERTIFICATE OF CORRECTION

PATENT NO. : 4,870,961
DATED : October 3, 1989
INVENTOR(S) : Gordon D. Barnard

It is certified that error appears in the above-identified patent and that said Letters Patent is hereby corrected as shown below:

Column 6, line 24, delete "manifold" and insert --manifolds-- therefor.

Claim 1, line 11, delete "aid" and insert --said-- therefor.

Claim 14, line 12, before "nebulizer" insert --a--.

Claim 14, line 29, after "connecting" and before "pressure insert --said nebulizer means passageway to the third--.

Signed and Sealed this

Twenty-fifth Day of September, 1990

Attest:

HARRY F. MANBECK, JR.

Attesting Officer     Commissioner of Patents and Trademarks